United States Patent [19]
Reinehr et al.

[11] Patent Number: 6,020,490
[45] Date of Patent: *Feb. 1, 2000

[54] PROCESS FOR THE PREPARATION OF HYDROXYPHENYL-1,3,5-TRIAZINES

[75] Inventors: Dieter Reinehr, Kandern, Germany; Jean-Pierre Bacher, Buschwiller, France

[73] Assignee: Ciba Specialty Chemicals Corporation, Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/591,044

[22] Filed: Jan. 25, 1996

Related U.S. Application Data

[63] Continuation of application No. 08/324,828, Oct. 18, 1994, abandoned.

[30] Foreign Application Priority Data

Oct. 22, 1993 [CH] Switzerland .............................. 3199/93

[51] Int. Cl.[7] .................................................. C07D 251/24
[52] U.S. Cl. .............................................................. 544/216
[58] Field of Search ............................................... 544/216

[56] References Cited

U.S. PATENT DOCUMENTS 3,118,887  1/1964  Hardy et al. ............................ 260/248

OTHER PUBLICATIONS

Ryabukhin et al., Synthesis of bis(o–hydroxyphenl)–1,3, 5–trianzines . . ., Chemical Abstracts, 99:22431, (1983).

Brunetti et al, Die Synthese von asymmetrisch substituierten o Hydroxyphenyl–s–triazinen, Helv. Chim. Acta, vol. 55, pp. 1566–1595, (1972).

E. M. Smolin and L. Rapoport's —Triazines and Derivatives, 1967, Interscience Publishers Inc. NY pp. 158–159.

Comprehensive Heterocyclic Chemistry vol. 3, Part 2B, A. John Boulton, et al. (1984).

Pinner, Ber. deutsch, Chem. Ges. 23, 2934–2941 (1980).

CA 99:22431, Chemical Abstract, 1983 Helv. Chim. Acta, 55 (5), 1566–95, 1972.

*Primary Examiner*—Richard L. Raymond
*Assistant Examiner*—Deepak R. Rao
*Attorney, Agent, or Firm*—Luther A. R. Hall; Michele A. Kovaleski; Kevin T. Mansfield

[57] ABSTRACT

There is disclosed a simple process for the preparation of hydroxyphenyl-1,3,5,-triazines of formula (1), which comprises reacting 1 mol of a salicyl compound of formula (2) with 2 (mol) of the benzamidine of formula (3). The novel triazines are useful AV absorbers for organic materials, in particular polyester fibre materials.

13 Claims, No Drawings

PROCESS FOR THE PREPARATION OF HYDROXYPHENYL-1,3,5-TRIAZINES

This application is a continuation of application Ser. No. 08/324,828, filed Oct. 18, 1994 now abandoned.

The present invention relates to a simple one-step process for the preparation of 2-hydroxyphenyl-1,3,5-triazines starting from benzamidines and o-hydroxycarboxylic acid derivatives, and to the use of the compounds prepared by said process as UV absorbers.

The reaction of amidines either with ethyl chloroformate or with phosgene to give 2-hydroxyphenyl-s-triazines is known, inter alia from A. Pinner, Chem. Ber. 23, 2934 (1890). The 2-hydroxyphenyltriazines can then be prepared therefrom in a two-step process. However, only modest yields are obtained with this process.

It has now been found that 2-hydroxyphenyl-1,3,5-triazines can be prepared in a simple one-step process and in good yield using simple starting compounds.

The process for the preparation of a 2-hydroxyphenyltriazine of formula

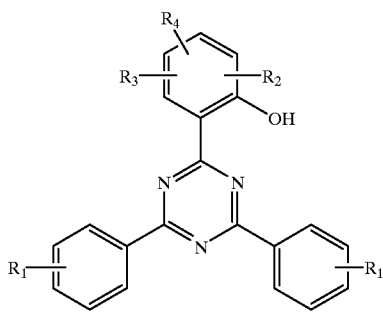

(1)

comprises reacting a salicyl compound of formula

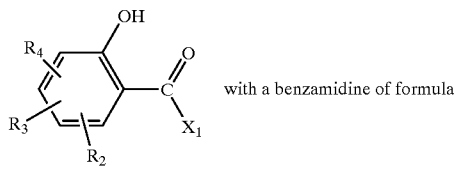

(2)

with a benzamidine of formula

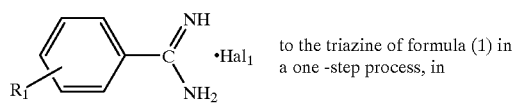

(3)

to the triazine of formula (1) in a one-step process, in which formulae above
$X_1$ is halogen or —$OR_5$,
$R_1$, $R_2$, $R_3$ and $R_4$ are each independently of one another hydrogen, halogen, hydroxy, $C_1$–$C_{18}$alkyl or $C_1$–$C_{18}$alkoxy,
$R_5$ is $C_1$–$C_3$alkyl, and
$Hal_1$ is halogen.

$C_1$–$C_{18}$Alkyl and $C_1$–$C_{18}$alkoxy are straight-chain or branched alkyl and alkoxy, typically methyl, ethyl, n-propyl, isopropyl, n-butyl, sec-butyl, tert-butyl, amyl, isoamyl or tert-amyl, heptyl, octyl, isooctyl, nonyl, undecyl, dodecyl, tetradecyl, pentadecyl, hexadecyl, heptadecyl or octadecyl, and, respectively, methoxy, ethoxy, propoxy, butoxy, pentoxy, hexoxy, heptyloxy, octyloxy, isooctyloxy, nonyloxy, undecyloxy, dodecyloxy, tetradecyloxy, pentadecyloxy, hexadecyloxy, heptadecyloxy or octadecyloxy.

Halogen is chloro, bromo or iodo. Chloro is preferred.

The starting compounds of formula (2) are unsubstituted or substituted salicylates or salicyloyl halides, for example methyl salicylate, ethyl salicylate or propyl salicylate, salicyloyl chloride or salicyloyl bromide, which compounds may be substituted in the phenyl nucleus by further halogen atoms or alkoxy or hydroxy groups, in accordance with the meaning of $R_2$, $R_3$ and $R_4$.

Preferred starting compounds of formula (2) are suitably methyl salicylate ($X_1$=—$OCH_3$) or salicyloyl chloride ($X_1$=Cl).

The starting compounds of formulae (2) and (3) can be used in in the process of this invention in different molar ratios.

The preferred molar ratio of compound of formula (2) to compound of formula (3) is 1:10 to 10:1.

If the starting compound of formula (2) is a salicylate ($X_1$=—$OCH_3$), the molar ratio of the compound of formula (2) to the compound of formula (3) is preferably 2:1 to 1:2.

If the starting compound of formula (2) is a salicyloyl halide, the molar ratio of the compound of formula (2) to the compound of formula (3) is 1:5 to 1:1,5, preferably 1:3 to 1:2.

The benzamidine of formula (3) is suitably benzamidine hydrobromide and, preferably, benzamidine hydrochloride. These compounds are usually used as solids wth an active substance content of c. 90–95%.

If the starting compound of formula (2) is a salicyloyl halide, at least the calculated amount of base will be added to neutralise the acid formed during the reaction. Suitable bases are organic as well as inorganic compounds, typically alkali metal hydroxides, preferably sodium or potassium hydroxide; aqueous ammonia solution; gaseous ammonia; alkali metal carbonates, preferably sodium or potassium carbonate; sodium acetate; tertiary amines such as pyridine, or trialkylamines, preferably triethylamine, N,N-dimethylcyclohexylamine, N,N-dimethylaniline; alkali metal alkylates, preferably sodium and potassium methylate or potassium tert-butylate.

The novel process is normally carried out by charging the salicyl compound and the benzamidine compound to an inert solvent Suitable inert solvents for the novel process are aliphatic hydrocarbons and mixtures thereof, for example cyclohexane, or aromatic hydrocarbons such as toluene or dimethyl acetamide, or mixtures of said solvents.

If the starting compound of formula (2) is a salicyloyl halide ($X_1$=Hal), a further, usually polar, solvent can be added to the reaction mixture, conveniently acetonitrile or dioxane.

The reaction times for the novel process are normally from 2 to 30 hours. Depending on whether the starting compound of formula (2) employed is a salicyloyl halide ($X_1$=Hal) or a salicylate ($X_1$=—$OR_5$), the reaction times may vary. If a salicylate is used, the reaction time is 4 to 30 hours, preferably 18 to 22 hours. If a salicyloyl halide is used, the reaction times are somewhat shorter and are from 2 to 20, preferably from 4 to 8, hours.

The reactions are usually slightly exothermic. However, a reaction temperature of 95° C. should not be exceeded, as by-products such as nitriles can be formed from the benzamidines at higher temperatures. In practice, the reaction is carried out in the temperature range from 60 to 95° C., preferably from 80 to 95° C.

The hydroxyphenyl-1,3,5-triazines are usually obtained in the form of crystalline compounds, so that a troublesome recystallisation is not necessary. When the reaction is complete, the product is washed with methanol and/or water and then dried in conventional manner.

The process of this invention makes it possible to prepare hydroxyphenyl-1,3,5-triazines in simple manner and in good yield.

The triazines obtained by the inventive process are useful UV absorbers for organic materials, in particular for polyester fibre materials.

The invention is illustrated by the following Examples, in which percentages are by weight.

Preparation of the hydroxyphenyl-1,3,5-triazines

EXAMPLE 1

69 g (0.4 mol) of benzamidine hydrochloride (91%) are added to c. 170 ml (200 g) of methyl salicylate. To this mixture are added 72 g (0.4 mol) of a 30% solution of sodium methylate and 170 ml of cyclohexane. With stirring, the reaction mixture is then heated to 90° C., whereupon c. 130 ml of a mixture of methanol-cyclohexane distills from the reaction mixture over 45 minutes. The distillation is discontinued and the reaction mixture is stirred for 22 hours at 90–95° C., cooled to 5° C. and filtered. The filter product is washed with 150 ml of methanol and then with 2 litres of water and dried at 120° C. in a drying oven, giving a pale yellow compound of formula

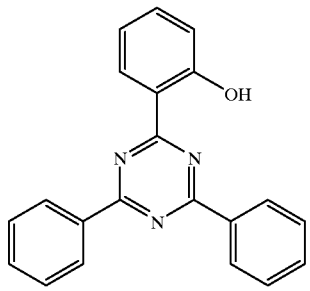

(101)

Yield: 47.5 g (73% of theory). m.p.: 247–248° C.

EXAMPLE 2

The process as described in Example 1 is repeated, but using 400 g of methyl salicylate (instead of 200 g). Working up gives 46 g of the compound of formula (101), corresponding to a yield of 70.7% of theory.

EXAMPLE 3

The process as described in Example 1 is repeated, but using 42 g (0.226 mol) of 4-methoxybenzamidine hydrochloride, 40 g (0.22 mol) of a 30% solution of sodium methylate and 33 g (0.22 mol) of methyl salicylate in a mixture of 100 ml of dimethyl acetamide/120 ml of cyclohexane. After a reaction time of 20 hours at 90 to 95° C. and subsequent working up, a pale yellow product of formula

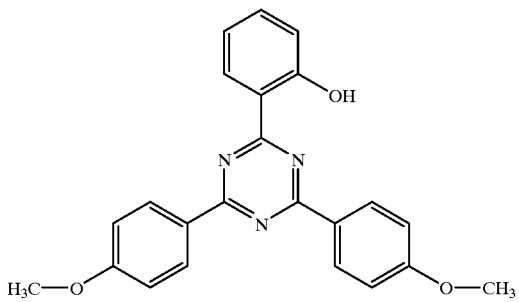

(102)

is obtained.

Yield: 30.6 g (72.2% of theory). m.p.: 205–206° C.

EXAMPLE 4

67.4 g (0.4 mol) of benzamidine hydrochloride (93%), 200 ml of acetonitrile and 61 g (0.6 mol) of triethylamine are stirred for 1 hour at room temperature. The mixture is then cooled to 0° C. and 31.3 g (0.2 mol) of salicyloyl chloride are added dropwise at 0–5° C. over 20 minutes, whereupon the suspension turns deep yellow. The suspension is stirred for 22 hours at room temperature, then heated for 22 hours to 75–80° C. and subsequently cooled to 60° C. Then 300 ml of methanol are added and, after cooling to 5° C., the precipitate is filtered with suction, washed with 200 ml of methanol and dried at 110° C. in a vacuum drying oven to give 49.7 g of the compound of formula (101), corresponding to a yield of 76.4% of theory; m.p.: 248–249° C.

EXAMPLE 5

The procedure as described in Example 4 is repeated, but using 200 ml of dioxane instead of 200 ml of acetonitrile. After a reaction time of 6.5 hours at 95° C. (instead of 22 hours at 75–80° C.), the compound of formula (101) is obtained in a yield of 49 g (75.3% of theory).

EXAMPLES 6 to 13

In accordance with the general procedure of Example 4, substituted salicyloyl chlorides are reacted with benzamidine hydrochloride or 4-methoxybenzamidine hydrochloride in comparable yields to give the corresponding triazines of the following structural formula (Table 1):

TABLE 1

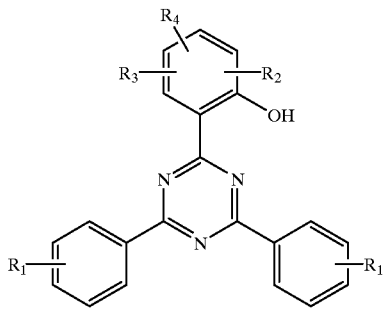

| Example | Compound of formula | R | $R_1$ | $R_2$ | $R_3$ | m.p. [° C.] |
|---------|---------------------|-----|--------|--------|-------|-------------|
| 6 | (103) | H | H | OH | H | 270–271 |
| 7 | (104) | H | H | $OCH_3$ | H | 203 |
| 8 | (105) | H | H | $CH_3$ | H | 237–238 |
| 9 | (106) | H | $CH_3$ | H | H | 207–208 |
| 10 | (107) | H | H | H | Cl | 222–223 |
| 11 | (108) | $OCH_3$ | $CH_3$ | H | H | 183–184 |
| 12 | (109) | $OCH_3$ | H | $CH_3$ | H | 198–199 |
| 13 | (110) | $OCH_3$ | H | H | Cl | 242–243 |

What is claimed is:

1. A process for the preparation of a 2-hydroxyphenyltriazine of the formula (1)

(1)

which comprises reacting a salicyl compound of the formula (2)

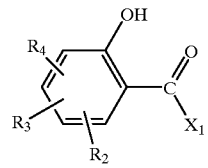

(2)

with a benzamidine of formula (3)

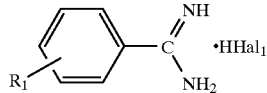

(3)

to form the compound of the formula (1) in a one-step process in the presence of a base selected from the group consisting of alkali metal alkylates, trialkylamines, aqueous ammonia and ammonia gas,
in which formulae above
  $X_1$ is halogen or $—OR_5$,
  $R_1$, $R_2$, $R_3$ and $R_4$ are each independently of one another hydrogen, halogen, hydroxy, $C_1$–$C_{18}$alkyl or $C_1$–$C_{18}$alkoxy,
  $R_5$ is $C_1$–$C_3$alkyl, and
  $Hal_1$ is halogen.

2. A process according claim 1, wherein $X_1$ is chloride or methoxy.

3. A process according to claim 1, wherein the molar ratio of the compound of formula (2) to the compound of the formula (3) is 1:10 to 10:1.

4. A process according to claim 3, wherein the molar ratio of the compound of formula (2) to the compound of formula (3) is 2:1 to 1:2 when $X_1$ is $—OR_5$.

5. A process according to claim 3, wherein the molar ratio of the compound of formula (2) to the compound of formula (3) is 1:3 to 1:2 when $X_1$ is halogen.

6. A process according to claim 1, wherein the base is selected from the group consisting of alkali metal alkylates and trialkylamines.

7. A process according to claim 1, wherein the reaction is carried out in the presence of an inert solvent.

8. A process according to claim 7, wherein the solvent is selected from cyclohexane, toluene, dimethyl acetamide or a mixture of said solvents.

9. A process according to claim 7, wherein acetonitrile or dioxane is used as additional solvent when $X_1$ in formula (2) is halogen.

10. A process according to claim 1, wherein the reaction time is from 2 to 30 hours.

11. A process according to claim 10, wherein the reaction time is from 4 to 30 hours when $X_1$ in formula (2) is $—OR_5$.

12. A process according to claim 10, wherein the reaction time is from 2 to 20 hours when $X_1$ in formula (2) is halogen.

13. A process according to claim 1, wherein the reaction temperature is in the range from 80 to 95° C.

* * * * *